(12) United States Patent
Cassimjee et al.

(10) Patent No.: US 10,793,848 B2
(45) Date of Patent: Oct. 6, 2020

(54) IMMOBILIZED PROTEINS AND USE THEREOF

(71) Applicant: EnginZyme AB, Stockholm (SE)

(72) Inventors: Karim Engelmark Cassimjee, Stockholm (SE); Jan-Erling Bäckvall, Stocksund (SE)

(73) Assignee: ENGINZYME AB, Solna (SE)

(*) Notice: Subject to any disclaimer, the term of this patent is extended or adjusted under 35 U.S.C. 154(b) by 0 days.

(21) Appl. No.: 15/112,206

(22) PCT Filed: Jan. 30, 2015

(86) PCT No.: PCT/SE2015/050108
§ 371 (c)(1),
(2) Date: Jul. 18, 2016

(87) PCT Pub. No.: WO2015/115993
PCT Pub. Date: Aug. 6, 2015

(65) Prior Publication Data
US 2016/0340667 A1    Nov. 24, 2016

(30) Foreign Application Priority Data

Jan. 31, 2014 (SE) ........................... 1450105
Jul. 2, 2014 (SE) ........................... 1450822

(51) Int. Cl.
*C12N 11/14* (2006.01)
*C07K 17/06* (2006.01)
(Continued)

(52) U.S. Cl.
CPC .............. *C12N 11/14* (2013.01); *C07K 1/22* (2013.01); *C07K 17/06* (2013.01); *C12N 11/08* (2013.01);
(Continued)

(58) Field of Classification Search
None
See application file for complete search history.

(56) References Cited

U.S. PATENT DOCUMENTS 4,632,904 A   12/1986 Lee
6,087,452 A    7/2000 Stewart
(Continued)

FOREIGN PATENT DOCUMENTS

CN    102260662 A   11/2011
CN    102998444 A    3/2013
(Continued)

OTHER PUBLICATIONS

Sabine A. Lauer and John P. Nolan, Development and Characterization of Ni-NTA-Bearing Microspheres, 2002, Cytometry, vol. 48, pp. 136-145.*
(Continued)

*Primary Examiner* — Michelle F. Paguio Frising
*Assistant Examiner* — Trent R Clarke
(74) *Attorney, Agent, or Firm* — Pearne & Gordon LLP (57) ABSTRACT

The invention relates to an immobilized protein material comprising a protein that is immobilized on a glass material or organic polymer through affinity tag binding. The glass material may be a porous glass material such as (hybrid) controlled porosity glass. The invention also relates to the use of an immobilized enzyme material as a heterogeneous biocatalyst in chemical synthesis. The invention further relates to a method for the immobilization of affinity tagged proteins on a glass material or organic polymer, and to a method for the purification and isolation of affinity tagged proteins by the immobilization of such proteins on a glass material or organic polymer.

20 Claims, 2 Drawing Sheets (51) Int. Cl.
- G01N 33/545 (2006.01)
- G01N 33/552 (2006.01)
- C07K 1/22 (2006.01)
- C12N 11/08 (2020.01)
- G01N 33/543 (2006.01)
- G01N 33/573 (2006.01)
- C12P 7/62 (2006.01)
- C12P 13/00 (2006.01)
- C12P 13/02 (2006.01)
- C12P 17/06 (2006.01)

(52) U.S. Cl.
CPC ............... *C12P 7/62* (2013.01); *C12P 13/001* (2013.01); *C12P 13/02* (2013.01); *C12P 17/06* (2013.01); *G01N 33/545* (2013.01); *G01N 33/54353* (2013.01); *G01N 33/552* (2013.01); *G01N 33/573* (2013.01); *Y02P 20/50* (2015.11)

(56) References Cited

U.S. PATENT DOCUMENTS

| | | |
|---|---|---|
| 2004/0011577 A1 | 1/2004 | Jung |
| 2009/0042745 A1 | 2/2009 | Minami et al. |

FOREIGN PATENT DOCUMENTS

| | | |
|---|---|---|
| WO | 9310162 A1 | 5/1993 |
| WO | 2009005631 A2 | 1/2009 |
| WO | 2010084996 A1 | 7/2010 |

OTHER PUBLICATIONS

Michelle E. Kimple, Allison L. Brill and Renee L. Pasker, Overview of Affinity Tags for Protein Purification, 2013, Curr. Protoc. Protein Sci., vol. 73, pp. 9.9.1-9.9.23 (Year: 2013).*

Darragh A. Gaffney, Sarah O'Neill, Mary C. O'Loughlin, Ulf Hanefeld, Jakki C. Cooney and Edmond Magner, Tailored adsorption of His6-tagged protein onto nickel(II)—cyclam grafted mesoporous silica, 2010, Chem. Commun., vol. 46, pp. 1124-1126 (Year: 2010).*

International Search Report dated May 18, 2015 for PCT/SE2015/050108.

Purebiotech LLC: "MPG Streptavidin I MPG (R) Avidin"; Middlesex NJ USA; http://www.purebiotechllc.com/mbpd/immob/immob.html, retrieved May 15, 2015, pp. 1-3.

Purebiotech LLC: "Controlled Pore Glass Products"; Middlesex, NJ USA; http://www.purebiotechllc.com/cpgp/index.html, retrieved May 15, 2015, pp. 1-2.

Engelmark-Cassimjee et al: "A general protein purification and immobilization method on controlled porosity glass: biocatalytic applications"; Chemical Communications (The Royal Society of Chemistry); vol. 50, No. 65; Jul. 3, 2014, pp. 9134-9137, XP055189428; Burlington House, London; ISSN: 1359-7345.

International Preliminary Report on Patentability dated May 30, 2016 for PCT/SE2015/050108.

Cassimjee, "Tools in Biocatalysis: Enzyme immobilisation on silica and synthesis of enantiopure amines", Licentiate Thesis, Royal Institute of Technology, Stockholm, 2010, pp. 1-27.

Schätzle, Sebastian, et al. "Rapid and sensitive kinetic assay for characterization of ω-transaminases." Analytical chemistry 81(19) (2009): 8244-8248.

Engström, Karin, et al. "Co-immobilization of an Enzyme and a Metal into the Compartments of Mesoporous Silica for Cooperative Tandem Catalysis: An Artificial Metalloenzyme." Angewandte Chemie 52 (2013): 14006-14010.

Kadow, Maria, et al. "Recombinant expression and purification of the 2, 5-diketocamphane 1, 2-monooxygenase from the camphor metabolizing Pseudomonas putida strain NCIMB 10007." AMB express 1(13) (2011): 1-8.

Ling, Daishun, et al. "A General Strategy for Site-Directed Enzyme Immobilization by Using NiO Nanoparticle Decorated Mesoporous Silica." Chem. Eur. J. 20(26) (2014): 7916-7921.

Tischer, Wilhelm, and Frank Wedekind. "Immobilized enzymes: methods and applications." Topics in Current Chemistry, vol. 200, Springer Verlag Berlin Heidelberg, 1999, 95-126.

Brena et al., "Immobilization of Enzymes: A Literature Survey", Methods in Biotechnology: Immobilization of Enzymes and Cells, 2013, third edition, pp. 15-31.

Lundqvist, et al., "Protein adsorption onto silica nanoparticles: conformational changes depend on the particles' curvature and the protein stability." Langmuir 20(24) (2004): 10639-10647.

Porath, Jerker, et al. "Metal chelate affinity chromatography, a new approach to protein fractionation." Nature 258 (1975): 598-599.

Hochuli, E., et al. "Genetic approach to facilitate purification of recombinant proteins with a novel metal chelate adsorbent." Bio/technology 6(11) (1988): 1321-1325.

Ljungquist, Charlotta, et al. "Immobilization and affinity purification of recombinant proteins using histidine peptide fusions." European Journal of Biochemistry 186(3) (1989): 563-569.

Cassimjee, Karim Engelmark, et al. "Silica-immobilized His6-tagged enzyme: Alanine racemase in hydrophobic solvent." Biotechnology and bioengineering 99(3) (2008): 712-716.

Cassimjee, Karim Engelmark, et al. "One-step enzyme extraction and immobilization for biocatalysis applications." Biotechnology Journal 6(4) (2011): 463-469.

Cassimjee, Karim Engelmark, et al. "Active site quantification of an ω-transaminase by performing a half transamination reaction." ACS Catalysis 1(9) (2011): 1051-1055.

Cassimjee, Karim Engelmark, et al. "Chromobacterium violaceum ω-transaminase variant Trp60Cys shows increased specificity for (S)-1-phenylethylamine and 4′-substituted acetophenones, and follows Swain-Lupton parameterisation." Organic & Biomolecular Chemistry 10(28) (2012): 5466-5470.

Rogalski, J., et al. "Immobilization of laccase from Cerrena unicolor on controlled porosity glass." Journal of Molecular Catalysis B: Enzymatic 6(1) (1999): 29-39.

Sandström, Anders G., et al. "Directed evolution of Candida antarctica lipase A using an episomaly replicating yeast plasmid." Protein Engineering Design and Selection 22(7) (2009): 413-420.

Engström, Karin, et al. "Mutated variant of Candida antarctica lipase B in (S)-selective dynamic kinetic resolution of secondary alcohols." Organic & Biomolecular Chemistry 9(1) (2011): 81-82.

Mutti, Francesco G., et al. "Amination of Ketones by Employing Two New (S)-Selective ω-Transaminases and the His-Tagged ω-TA from Vibrio fluvialis." European Journal of Organic Chemistry 2012(5) (2012): 1003-1007.

Kadow, Maria, et al. "Functional assembly of camphor converting two-component Baeyer-Villiger monooxygenases with a flavin reductase from *E. coli*." Applied Microbiology and Biotechnology 98(9) (2014): 3975-3986.

Chikh, et al., "Attaching histidine-tagged peptides and proteins to lipid-based carriers through use of metal-ion-chelating lipids," Biochimica et Biophysica Acta, 2002, vol. 1567, pp. 204-212.

Brady, et al., "Advances in enzyme immobilisation", Biotechnol Lett 31, pp. 1639-1650 (2009).

Liu, et al., "Combined Biosynthetic Pathway for De Novo Production of UDP-Galactose:Catalysis with Multiple Enzymes Immobilized on Agarose Beads", ChemBioChem, 3, pp. 348-355 (2002).

Magner, "Immobilisation of enzymes on mesoporous silicate materials", Chem. Soc. Rev., pp. 1-10 (2013), DOI: 10.1039/c2cs35450k.

Pessela, et al., "One-Step Purification, Covalent Immobilization, and Additional Stabilization of a Thermophilic Poly-His-Tagged B-Galactosidase from *Thermus* sp. Strain T2 by using Novel Heterofunctional Chelate-Epoxy Sepabeads", Biomacromolecules, vol. 4, No. 1, pp. 107-113 (2003).

Uhlig, et al., "Pseudomorphic Transformation of Porous Glasses into Micelle-Templated Silica", Chem. Ing. Tech., vol. 89, No. 7, pp. 863-875 (2017).

Ryan, et al., Comparison of Chelating Agents Immobilized on Glass with Chelex 100 for Removal and Preconcentration of Trace Copper(II), Talanta, vol. 32, No. 9, pp. 859-863 (1985).

(56) References Cited

OTHER PUBLICATIONS

Fang, et al., Immobilized enzyme reactors in HPLC and its application in inhibitor screening: A review, Journal of Pharmaceutical Analysis, 2012, 2(2), pp. 83-89.

Rothstein, et al., Solid-Phase Supports for Oligo Synthesis: New High-Performance Tools Help Meet Demand for Higher Volume and Lower Cost Manufacturing, GEN, 2012, vol. 32, No. 9, 3 pages.

M. Hasanuzzaman, et al., "Production and Treatment of Porous Glass Materials for Advanced Usage", Reference Module in Materials Science and Materials Engineering, 2016, pp. 1-13; doi: 10.1016/B978-0-12-803581-8.03999-0.

Michal Kruk et al., "Characterization of the Porous Structure of SBA-15", Chem. Mater., 2000, vol. 12, pp. 1961-1968.

Jörg P. Thielemann, et al., "Pore structure and surface area of silica SBA-15: influence of washing and scale-up", Beilstein Journal of Nanotechnology, 2011, vol. 2, pp. 110-118.

Dongyuan Zhao, et al., "Triblock Copolymer Syntheses of Mesoporous Silica with Periodic 50 to 300 Angstrom Poores", Science, 1998, vol. 279, pp. 548-552.

ZetA Partikelanalytick GmbH, "Boron Elemental Analysis of CPG samples," May 2, 2019, one page.

Thompson et al., "A generic platform for the immobilisation of engineered biocatalysts," Tetrahedron, vol. 75, pp. 327-334, Dec. 6, 2018.

Kumar et al., "A top-down approach to classify enzyme functional classes and sub-classes using random forest," EURASIP Journal on Bioinformatics and Systems Biology 2012, 2012:1, doi:10.1186/1687-4153-2012-1, available at http://bsb.eurasipjournals.com/content/2012/1/1, 2012.

Extended European Search Report for European Application No. 19192953.8 dated Jan. 9, 2020.

Sari et al., "Polystyrene Attached Pt(IV)-Azomethine, Synthesis and Immobilization of Glucose Oxidase Enzyme"; Int. J. Mol. Sci., vol. 13, pp. 11870-11880, Sep. 19, 2012.

\* cited by examiner

IMMOBILIZED PROTEINS AND USE THEREOF

TECHNICAL FIELD

The invention relates to an immobilized protein material comprising a protein that is immobilized on a glass material or organic polymer through affinity tag binding. The glass material may be a porous glass material such as (hybrid) controlled porosity glass. The invention also relates to the use of an immobilized enzyme material as a heterogeneous biocatalyst in chemical synthesis. The invention further relates to a method for the immobilization of affinity tagged proteins on a glass material or organic polymer, and to a method for the purification and isolation of affinity tagged proteins by the immobilization of such proteins on a glass material or organic polymer.

BACKGROUND ART

Proteins are large biological molecules made up of one or several linear chains of amino acid residues. Enzymes are a specific group of proteins which serve as biological catalysts in the metabolism of all living cells. As such, enzymes are able to transform organic molecules into different molecules. Because of the specific three-dimensional structure of each particular enzyme, only very few organic molecules will interact with the enzyme's active site in such a way that transformation can take place. Enzymes are therefore usually highly selective catalysts, and the use of enzymes as catalysts in synthetic organic chemistry is for that reason very appealing. However, since enzymes are biological molecules evolved for a cell environment, they are often unsuited for other environments. When used in organic solvents, enzymes tend to aggregate and often unfold (i.e., denature). It is therefore attractive to immobilize enzymes on solid support and to use them as catalysts in this immobilized state, as this may improve the stability of the enzyme, allow for reaction conditions which the enzyme normally would not tolerate and furthermore facilitate the separation from the reaction mixture and recovery of the material.

Immobilization of enzymes on solid support has been accomplished using different techniques and different solid supports (Tischer and Wedekind, "Immobilized Enzymes: Methods and Applications", Topics in Current Chemistry, 1999, vol. 200, pp. 95-126; Brena and Batista-Viera, "Immobilization of Enzymes: A Literature Survey", Methods in Biotechnology: Immobilization of Enzymes and Cells, 2006, second edition, pp. 15-30).

Adsorption of enzymes to solid surfaces can lead to undesired interactions between the enzyme and the solid support. It has been shown that protein adsorption onto silica nanoparticles may lead to changes in the secondary structure of the protein, which can result in deactivation of the enzyme (Lundqvist et al., Langmuir 2004, vol. 20, pp. 10639-10647). It is therefore important that the solid support does not interfere with the structure and the activity of the immobilized enzymes.

Immobilized metal ion affinity chromatography (IMAC) is a technique for purification of proteins which is based on the affinity of proteins for metal ions such as $Fe^{2+}$, $Cu^{2+}$, $Zn^{2+}$, $Ni^{2+}$ and $Co^{2+}$. The metal ions are immobilized on an agarose gel and can selectively adsorb histidine- and cysteine-containing proteins (Porath et al., Nature 1975, vol. 258, pp. 598-599). An improved version of this technique uses recombinant proteins containing a fused polyhistidine peptide. As the polyhistidine peptide has a much higher affinity for the immobilized metal ions than a single histidine residue, the level of purification that can be achieved is much higher (Hochuli et al., Nat. Biotechnol. 1988, vol. 6, pp. 1321-1325; Ljungquist et al., Eur. J. Biochem. 1989, vol. 186, pp. 563-569). Although this technique can be successfully applied in chromatographic procedures for purification and isolation of proteins, the gel-immobilized enzymes are less suitable as heterogeneous catalysts in organic synthesis. The IMAC technique is furthermore primarily restricted to aqueous conditions.

In attempts to prepare heterogeneous catalysts, the IMAC-based principle of affinity tag binding has been applied to the immobilization of polyhistidine-tagged enzymes on modified silica (Cassimjee et al., Biotechnol. Bioeng. 2008, vol. 99, pp. 712-716; Cassimjee et al., Biotechnol. J. 2011, vol. 6, pp. 463-469). This worked well for *Candida antarctica* lipase B (CalB), but other, less stable enzymes were found to be deactivated in the presence of silica, especially in the presence of organic solvents. It is known in the literature that silica nanoparticles have a destabilizing effect on proteins (Lundqvist et al., Langmuir 2004, vol. 20, pp. 10639-10647).

Controlled porosity glass (CPG) is another material that has been used for the immobilization of enzymes. The CPG is usually treated with 3-aminopropyltriethoxysilane, and the enzymes are thereafter allowed to bind to the aminopropyl-CPG through lysine residues present on the enzymes' surface, using glutaraldehyde as a cross-linking agent. This results in a nonspecific binding of the enzyme to the CPG, often with concomitant loss of the enzymatic activity. A further drawback of this method is that the enzyme to be immobilized must be purified from other enzymes prior to the immobilization step, in order to avoid the immobilization of a mixture of different enzymes on the CPG.

The immobilization of enzymes on CPG using organotitanates (U.S. Pat. No. 4,632,904) or using polysaccharide layers and 1,1'-dicarbonyldiimidazole (Rogalski et al., J. Mol. Catal. B: Enzym. 1999, vol. 6, pp. 29-39) has also been disclosed.

Engstrom et al. (Angew. Chem. Int. Ed. 2013, vol. 52, pp. 14006-14010) disclose a hybrid catalyst in which *Candida antarctica* lipase B and a nanopalladium species are co-immobilized into the compartments of mesoporous silica.

The use of enzymes as catalysts in chemical industry, i.e. biocatalysis, is key to achieving higher sustainability, less toxic waste and higher cost efficiency. However, the high costs of enzymes and the frequently observed loss of activity upon immobilization of the enzyme on solid support are obstacles in this development. A standardized and generally workable procedure for enzyme immobilization, which would allow the enzyme to be re-used, would be highly desirable. Despite progress made in recent years, there still is no general and simple method for the preparation of heterogeneous catalysts by immobilization of enzymes. There is therefore a continued need for improved methods for the immobilization of enzymes on a solid support, and for stable heterogeneous biocatalysts which can be applied in organic synthesis under both aqueous and organic reactions conditions.

BRIEF DESCRIPTION OF THE DRAWINGS

The chelation of the cobalt ion to the 2,4-dihydroxyphenyl residue and the polyhistidine-tagged enzyme is schematically depicted.

DETAILED DESCRIPTION OF THE INVENTION

It has surprisingly been discovered that by immobilizing proteins on a porous glass material or a porous organic polymer through affinity tag binding, an immobilized protein material is obtained having improved properties with respect to stability of the immobilized proteins, and wherein the biological function of the proteins is maintained. Preparations of immobilized enzymes were found to have a high catalytic activity, which makes them useful in biocatalysis.

According to the invention, a protein containing an affinity tag is immobilized by being bound to a specific group on an affinity matrix attached to the porous glass material or the porous organic polymer. Because of the high binding affinity of the affinity tag for the specific group on the matrix, the binding of the protein to the matrix is both strong and highly specific. The invention thus provides general methods for the purification and immobilization of proteins, such as enzymes.

In a first aspect, the invention relates to an immobilized protein material comprising a carrier and at least one protein immobilized on the carrier, wherein the carrier comprises a carrier material to which an affinity matrix is attached, said carrier material being chosen from the group consisting of:
 (a) controlled porosity glass (CPG);
 (b) hybrid controlled porosity glass (Hybrid CPG); and
 (c) a porous organic polymer;
and wherein the at least one protein contains an affinity tag and is immobilized on the carrier through specific affinity binding to the affinity matrix.

The immobilization of proteins on the carrier via an affinity tag offers the advantage of a specific binding of the proteins on a predefined site. At the same time, however, the immobilization method is generally applicable to many different proteins. The affinity tag that is used in the invention may be any tag that is able to specifically bind to a matrix for which it has affinity. The affinity binding may be the result of, e.g., van der Waals' interaction, hydrogen bonding, ionic bonding or hydrophobic interaction. In any case, the affinity binding should be strong enough to allow the affinity tag and the matrix to remain tightly bonded to each other at least until certain specific conditions are applied in order to dissociate the affinity tag from the matrix.

In another aspect, the invention relates to a carrier for the immobilization of proteins, comprising a carrier material to which an affinity matrix is attached, said carrier material being chosen from the group consisting of:
 (a) controlled porosity glass (CPG);
 (b) hybrid controlled porosity glass (Hybrid CPG); and
 (c) a porous organic polymer;
 and wherein the proteins are immobilized on the carrier through specific affinity binding to the affinity matrix.

The protein to be immobilized on the carrier may be any protein containing an affinity tag, such as a (recombinant) protein or enzyme containing an affinity tag. Preferably, the protein is an enzyme containing an affinity tag. It is to be understood that the tag should have specific affinity for the affinity matrix attached to the carrier.

A number of affinity tags and corresponding matrices are known in the art. Examples of affinity tags that may be useful in the invention, and the corresponding groups on the matrix, are listed in the table below:

| Affinity tag | Corresponding groups on matrix |
| --- | --- |
| polyhistidine tag | chelated metal ions, e.g. $Fe^{2+}$, $Fe^{3+}$, $Co^{2+}$, $Ni^{2+}$, $Cu^{2+}$, $Zn^{2+}$ |
| glutathione S-transferase (GST) | glutathione |
| chitin binding protein (CBP) | chitin |
| maltose binding protein (MBP) | cross-linked amylose |
| FLAG-tag | Anti-FLAG monoclonal antibody |
| avidin | biotin |
| streptavidin | biotin |

In a preferred embodiment, the affinity tag on the protein is a polyhistidine tag and the affinity matrix attached to the carrier contains a chelated metal ion. The chelated metal ion is preferably a metal ion selected from the group consisting of $Fe^{2+}$, $Fe^{3+}$, $Co^{2+}$, $Ni^{2+}$, $Cu^{2+}$ and $Zn^{2+}$, and is more preferably selected from the group consisting of $Fe^{3+}$, $Ni^{2+}$ and $Co^{2+}$. In a preferred embodiment, the chelated metal ion is $Co^{2+}$. In another preferred embodiment, the chelated metal ion is $Fe^{3+}$.

The choice of the chelated metal ion may be dependent on the intended use. For instance, if the carrier is to be used for the purification and isolation of an affinity tagged protein, the binding of the enzyme to the carrier should be reversible. In such cases, it is preferred that the chelated metal ion is $Ni^{2+}$ or $Co^{2+}$, and most preferably $Co^{2+}$. These metal ions bind strong enough for immobilizing a polyhistidine-tagged enzyme, but are also capable of releasing the immobilized enzyme when specific conditions are applied, such as treatment with a buffered solution containing imidazole or ethylenediaminetetraacetate (EDTA).

For the use of immobilized enzymes in heterogeneous biocatalysis, a strong binding of the enzyme to the carrier is desirable. In such cases, it is preferred that the chelated metal ion is $Co^{2+}$ or $Fe^{3+}$, and most preferably $Fe^{3+}$, since this results in particularly strong binding of the polyhistidine tag to the carrier. As is demonstrated in the examples, leaching of either enzyme or metal ion from immobilized protein material comprising $Fe^{3+}$ as the chelated metal ion is almost negligible. The absence of leaching allows the immobilized protein material (the biocatalyst) to be used in catalytic amounts. The use of catalytic amounts is particularly important in continuous flow reactions.

A further advantage of $Fe^{3+}$ as the chelated metal ion is that this metal is non-toxic. The resulting immobilized protein material may therefore be safely applied e.g. in the food industry.

The matrix for the affinity-tagged protein is attached to the surface of the carrier through an appropriate linker. The surface of controlled porosity glass (CPG) contains free silanol (Si—OH) groups, which can be attached to a linker molecule via a covalent bond. Typically, the surface is reacted with a bifunctional alkyl silane linker molecule (the chain length and structure of which may vary), whereby the silicon atom is covalently bonded with the glass surface silanol groups and wherein the terminal group of the silane is a functional group, such as an aldehyde, an amine, an epoxy group, a halide, or a carboxylic acid derivative. The appropriate functional group that should be used will depend on the nature of the matrix to be attached to the surface of theCPG. Methods for attaching the matrix to the surface of the CPG through an appropriate linker are known to the skilled in the art.

CPG is a robust and inert glass material that can be produced as particles of size-controlled macro- or mesopores. The sharp pore size distribution of CPG can be varied for pore sizes of about 10 to 300 nm diameters. This provides a favorable microenvironment without complications due to steric hindrance. The interconnecting pore structure results in low solution flow resistance and facilitates the mass transfer of reactants and products throughout the material. The rigid structure of CPG provides a rugged, noncompressible medium suitable for high throughput reactor designs and linear scale up at high flow rates.

The material displays limited swelling in solvents and is chemically and dimensionally stable in most organic media and aqueous environments at pH below 10.

Conventional CPG exhibits a ligand loading capacity that is inversely related to its pore size. Thus, a CPG support of a large pore size cannot be loaded with as much protein as a CPG support of a smaller pore size. This is partially due to the inverse relationship between pore size and surface area, and partially due to surface accessible silanol groups serving as functionalization moieties having a defined density per unit of surface area, approximately 4.5 µmol/m². Conventional CPG displays a non-uniform silanol distribution where sterically hindered silanol sites may not serve as functional attachment points.

Hybrid controlled porosity glass (Hybrid CPG, or HybCPG) is a variant of CPG wherein the interior and exterior surfaces of the CPG are coated with an approximately 10 nm film of a crosslinked organic polymer, as is described in WO 2009/005631. The polymeric coating on the Hybrid CPG may contain functional groups, such as aldehydes, amino groups, epoxy groups, halides, carboxylic acids and esters, or mixtures thereof, to which a matrix can be attached. Methods for attaching a matrix to an appropriate functional group are known to those skilled in the art.

Hybrid CPG offers certain advantages over conventional CPG. As a result of the polymer coating, the dependence between loading and pore size can be minimized and the spacing between functionalization sites can be more accurately and uniformly controlled. Hybrid CPG as carrier material for protein immobilization may offer additional benefits, because the design of the polymer coating can be tailored in order to provide surface characteristics that are desired or required for a given application. For instance, a homogeneous polymer such as polystyrene will produce a more hydrophobic carrier surface, while a homogeneous polymer such as polyacrylonitrile will produce a more hydrophilic carrier surface. By using mixtures of two or more different polymers, a co-polymeric coating may be obtained wherein the characteristics of the carrier surface are specifically adapted for a given application. The thin layer coatings allow some degree of microscopic swelling in organic solvents, but without bulk expansion of the Hybrid CPG bed or an increase in back pressure. The coatings also allow the use of Hybrid CPG in aqueous environments above pH 10.

Throughout the remainder of the description and the appended claims, any reference to CPG is to be interpreted as including both (conventional) CPG and Hybrid CPG, unless specifically indicated otherwise.

Other carrier materials than CPG and HybCPG may be desired due to reasons such as higher cost efficiency or specific process requirements. Such materials include porous organic polymer (plastic) materials. These polymers are functionalized with functional groups such as aldehydes, amino groups, epoxy groups, halides, carboxylic acids or esters, or mixtures thereof, to which a matrix can be attached. Methods for attaching a matrix to an appropriate functional group are known to those skilled in the art. The functionalized plastics can be produced as porous particles with limited swelling. Suitable organic polymers may be based on monomers such as styrene, ethylene, propylene, acrylic acid, methacrylic acid, methyl acrylate and methyl methacrylate. Examples of such organic polymers include functionalized polyethylene, ultra-high molecular weight polyethylene (UHMWPE), high-density polyethylene (HDPE), polypropylene (PP), polytetrafluoroethylene (PTFE), and polyvinylidene fluoride (PVDF), polystyrene, polymethacrylate and poly(methyl methacrylate). In a preferred embodiment, the porous organic polymer is functionalized polystyrene or functionalized polymethacrylate.

The attachment of affinity tagged proteins to HybCPG described herein demonstrates the possibility of using porous organic polymer carriers, since the porous surface in HybCPG is an organic polymer per se. HybCPG largely maintains the incompressible and non-swelling nature of CPG while the surface properties of organic polymers can be utilized. When the rigidity of CPG is not needed it is plausible that the organic polymer alone is a better choice. The method of applying an affinity tag attachment to such materials is therefore demonstrated herein.

Figure 1:
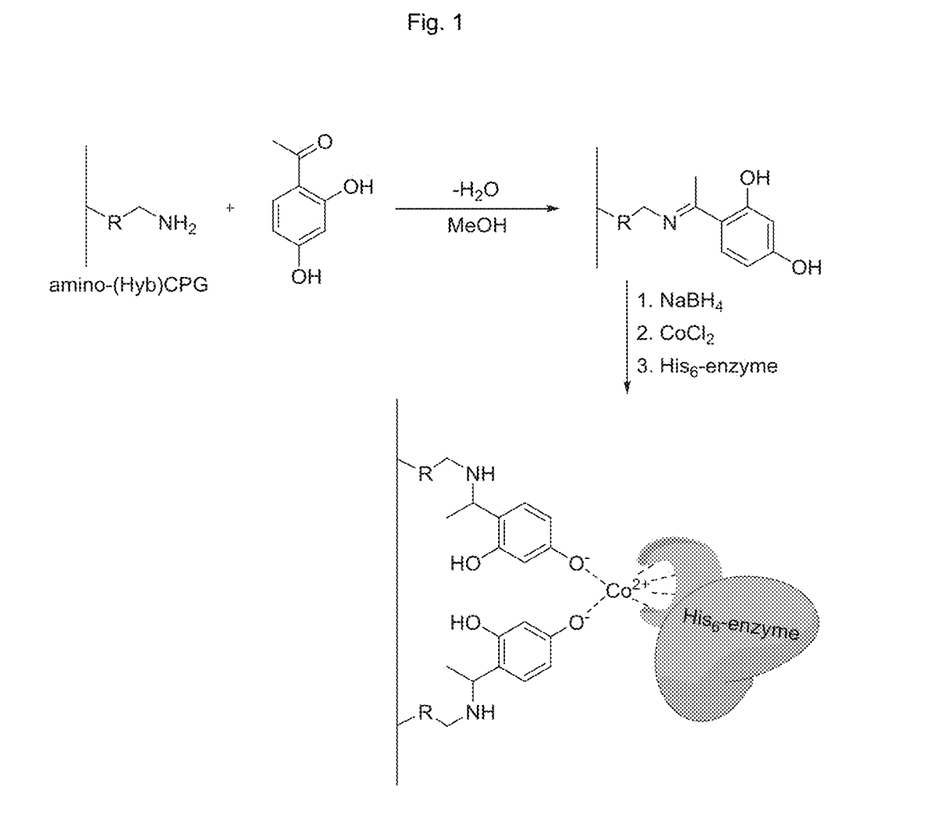
FIG. 1 shows the preparation of immobilized enzyme CPG-material from amino-(Hyb)CPG, using polyhistidine-tagged enzyme and $Co^{2+}$ as the chelated metal. The group R is a suitable linker, and varies between the CPG products.

CPG-immobilized protein material can easily be produced in only a few steps, starting from either amino-CPG or amino-HybCPG, as outlined in FIG. 1. For instance, the CPG materials can be treated with 2,4-dihydroxyacetophenone, thereby linking the phenyl group to the CPG via an imine. If desired, the imine functionality can thereafter be reduced to the corresponding amine using an appropriate reducing agent, such as e.g. sodium borohydride, sodium cyanoborohydride or lithium aluminum hydride. A chelated metal ion, such as $Co^{2+}$ or $Fe^{3+}$, can subsequently be introduced by suspension of the material in an aqueous solution of $CoCl_2$ or $FeCl_3$, respectively. After drying, the obtained material can directly be used as a binding matrix for one or more polyhistidine-tagged proteins.

An immobilized protein material wherein the carrier material is an organic polymer can be produced in a similar way as described above for CPG and HybCPG.

The high affinity of the polyhistidine tag for metal ions such as $Co^{2+}$ or $Fe^{3+}$ allows the immobilization of polyhistidine-tagged proteins to be performed from crude solutions containing the proteins without the need for extensive purification of the solution prior to the immobilization step. Organic material that does not contain a polyhistidine tag will bind to the chelated metal ions only weakly, or not at all, and will be easily removed from the final immobilized proteins material by washing with e.g. water or buffered aqueous solutions. Thus, if the polyhistidine-tagged protein is prepared by intracellular overexpression, the protein immobilization may be performed directly from the cell lysate. Alternatively, if the polyhistidine-tagged protein is secreted by the host organism, the protein immobilization may be performed directly from the cell culture supernatant.

Thus, in another aspect, the invention relates to a method for the immobilization of an affinity tagged protein, comprising the steps of i) immobilizing the affinity-tagged protein on a carrier comprising a carrier material to which an affinity matrix is attached, said carrier material being chosen from the group consisting of:
  (a) controlled porosity glass (CPG);
  (b) hybrid controlled porosity glass (Hybrid CPG); and
  (c) porous organic polymers; and
ii) optionally washing the immobilized protein material with water or an appropriate buffer.

In yet a further aspect, the invention provides a method for the preparation of an immobilized protein material, said method comprising:
  i) providing a carrier material containing amino groups, said carrier material being chosen from the group consisting of:
    (a) controlled porosity glass (CPG);
    (b) hybrid controlled porosity glass (Hybrid CPG); and
    (c) a porous organic polymer;
  ii) reacting the carrier material with 2,4-dihydroxyacetophenone, thereby linking a dihydroxyphenyl group to the carrier material;
    iii) forming a chelate complex between the dihydroxyphenyl group and a metal ion capable of binding a polyhistidine-tagged protein; and
    iv) binding a polyhistidine-tagged enzyme to the carrier material comprising said metal ion.

Optionally, the method for the preparation of an immobilized protein material as described above further comprises binding a transition metal nanoparticle to the carrier material.

In one embodiment, the carrier is controlled porosity glass (CPG). In another embodiment, the carrier is hybrid controlled porosity glass (Hybrid CPG). In yet another embodiment, the carrier is a porous organic polymer.

In a preferred embodiment, the method comprises the immobilization of affinity-tagged proteins on CPG or Hybrid CPG. In another preferred embodiment, the affinity-tagged protein is a polyhistidine-tagged enzyme and the affinity matrix contains a chelated metal ion. In a more preferred embodiment, the method comprises the immobilization of polyhistidine-tagged enzymes on CPG or Hybrid CPG, wherein the chelated metal ion used is $Co^{2+}$ or $Fe^{3+}$.

In another aspect the invention provides an immobilized protein material obtainable by the method as described above.

Dissociation of the bound protein can be achieved using standard IMAC methods. The bound protein may for instance be released from the carrier by lowering the pH or by adding a competitive molecule having equal or higher affinity for the chelated metal ions than the polyhistidine group, such as by applying a buffered solution containing imidazole or ethylenediaminetetraacetate (EDTA). After dissociation of the purified proteins from the carrier, the polyhistidine tag may be removed from the proteins, if necessary, by techniques known in the art, e.g. by cleaving the affinity tag with an appropriate enzyme such as a specific protease, thereby obtaining the pure and tag-less protein.

Thus, in yet another aspect, the invention relates to a method for the purification and isolation of an affinity tagged protein, comprising the steps of
  i) immobilizing an affinity-tagged protein on a carrier comprising a carrier material to which an affinity matrix is attached, said carrier material being chosen from the group consisting of:
    (a) controlled porosity glass (CPG);
    (b) hybrid controlled porosity glass (Hybrid CPG); and
    (c) porous organic polymers;
  ii) optionally washing the immobilized protein material with water or an appropriate buffer; and
  iii) dissociating the purified protein from the affinity matrix.

The immobilization step may be performed in an appropriate buffer. If necessary, the immobilized protein material may thereafter be washed with water or an appropriate buffer in order to remove any unbound proteins and other, undesired compounds from the immobilized protein material. Dissociation of the purified protein from the affinity matrix may be achieved by applying conditions that are appropriate for the particular affinity tag. Appropriate conditions for the dissociation of the different affinity tags are known in the art.

The method may optionally comprise the additional step of iv) removing the affinity tag from the purified protein.

In a preferred embodiment, the method comprises the purification and isolation of affinity-tagged proteins on CPG or Hybrid CPG. In another preferred embodiment, the affinity-tagged protein is a polyhistidine-tagged enzyme and the affinity matrix contains a chelated metal ion. In a more preferred embodiment, the method comprises the purification and isolation of polyhistidine-tagged enzymes on CPG or Hybrid CPG, wherein the chelated metal ion used is $Co^{2+}$.

If the proteins immobilized on the carrier, as described above, are enzymes, they contain an active site that is able to catalyze a chemical reaction. As such, the immobilized enzyme material is potentially useful as a biocatalyst in organic synthesis. Therefore, in another aspect, the invention relates to the use of an immobilized enzyme material as disclosed herein as a heterogeneous biocatalyst, for instance in synthetic organic transformations. The invention further provides a method for catalyzing an enzyme-catalyzed reaction, comprising providing an immobilized protein material according to the invention, and bringing the said immobilized protein material into contact with at least one substrate upon which an enzyme, which is immobilized on the carrier, is capable of acting.

The immobilization of enzymes on the carrier through affinity tag binding, as disclosed herein, improves the stability of the enzymes used. It has been found that the immobilized enzymes tolerate both aqueous conditions as well as a range of different organic solvents. This enables the immobilized enzymes materials to be used in reaction conditions under which the free, non-immobilized enzymes not would have been stable. It is possible that the immobilized enzyme material also may be used in a wider pH range than the free, non-immobilized enzymes would have tolerated.

When enzyme is bound from a crude (unpurified) preparation, the resulting immobilized protein material consists of enriched enzyme. Since the native activity of the enzyme method is retained, the immobilized preparation displays a higher catalytic activity per protein mass than the initial, non-immobilized protein material.

Another advantage of the present invention is that the immobilized enzyme material easily can be recycled. Since the immobilized enzyme material is a heterogeneous catalyst, the material can simply be collected from the reaction mixture by filtration. The material can thereafter be re-used in a further reaction, if necessary after purification of the material. Especially for enzymes that are expensive and/or difficult to cultivate, the possibility of recycling the immobilized enzyme material is an important aspect.

The enzyme that is immobilized on the carrier may be any enzyme that is useful as a biocatalyst in organic synthetic transformations, including, but not limited to, enzymes acting as oxidoreductases, transferases, hydrolases, lyases, isomerases and ligases. Thus, the immobilized enzyme materials may be used as heterogeneous biocatalysts in any organic reaction wherein the immobilized enzyme is able to specifically catalyze the reaction. Examples of such biocatalytic reactions include, but are not limited to, enzymatic oxidation and reduction reactions, enzymatic hydrolysis reactions and enzymatic isomerization reactions. Particularly useful biocatalytic reactions are enantioselective reactions. Specific examples of biocatalytic reactions include selective acylations of alcohols or amines with lipase, transaminations with w-transaminase, monooxygenations with CYP P450 or Baeyer-Villiger monooxygenase, oxidations of alcohols or reductions of ketones/aldehydes with alcohol dehydrogenase, and oxidations of amines with monoamine oxidase.

In one embodiment, two or more different enzymes may be immobilized onto the carrier, wherein each of the different enzymes is able to catalyze a different reaction. It may then be possible to use the material containing two or more different immobilized enzymes as a heterogeneous biocatalyst in a multi-step or cascade reaction. Such a cascade reaction may for instance be a reaction wherein two or more enzyme-catalyzed reactions are performed on a substrate in two or more subsequent steps (i.e., a reaction wherein a substrate for a first enzyme is transformed into a substrate for a second enzyme, and so on), such as a transamination reaction by an ω-transaminase followed by an acylation reaction by a lipase. Alternatively, such a cascade reaction may be a reaction wherein a substrate is transformed by a first enzyme and wherein a co-factor for the first enzyme is regenerated by a second enzyme, such as the selective/specific reduction of a ketone/aldehyde by alcohol dehydrogenase with the concomitant regeneration of consumed NADH by formate dehydrogenase.

When two or more different enzymes are immobilized onto the carrier, it is convenient if the different enzymes contain the same affinity tag, such as a polyhistidine tag. As the binding affinity for the chelating metal ion is equal for each of the enzymes, the different enzymes will bind equally strong to the carrier. Theoretically, therefore, when using equal amounts of n different enzymes having the same affinity tag, the amount of each different enzyme on the carrier will be 1/n (not taking into account any diffusion effects).

For cascade reactions using an immobilized protein material with two or more different immobilized enzymes, and wherein the different enzymes show a difference in catalytic activity, it may be advantageous to immobilize larger amounts of the enzyme(s) having lower catalytic activity, in comparison to the amount of enzyme having the higher catalytic activity. This will speed up the rate-determining step, and increase the overall rate of the reaction cascade.

Alternatively, cascade reactions may be performed by mixing one or more different immobilized enzyme materials in desired ratios.

In another aspect, the invention provides a method for catalyzing an enzyme-catalyzed multi-step or cascade reaction. In this aspect, the method comprises providing an immobilized protein material comprising two or more immobilized enzymes, according to the invention, and bringing the said immobilized protein material into contact with at least one substrate upon which the enzymes, which are immobilized on the carrier, are capable of acting.

Figure 2:
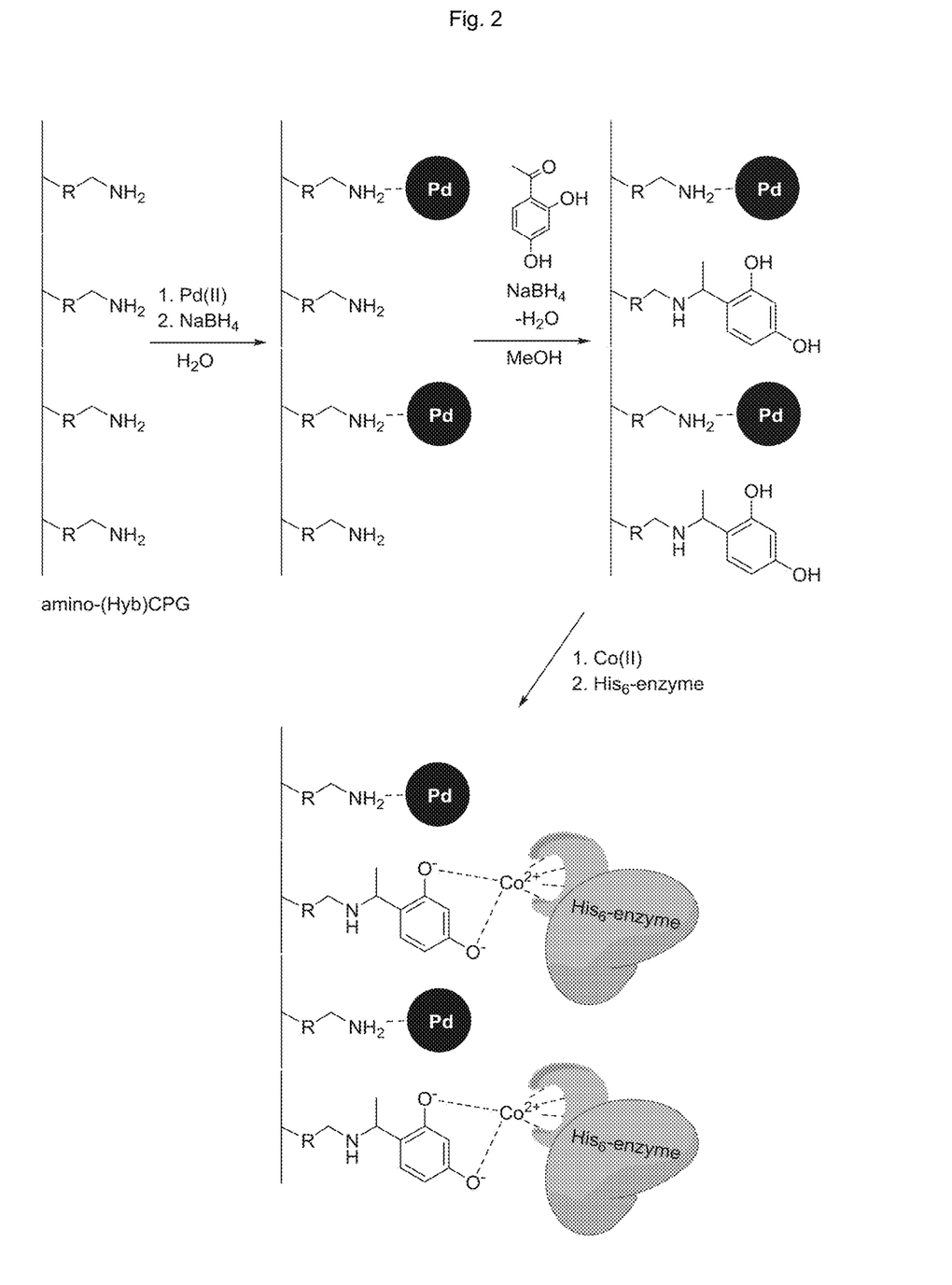
FIG. 2 shows the preparation of immobilized enzyme- and metal nanoparticle containing CPG-material from amino-(Hyb)CPG, using polyhistidine-tagged enzyme, $Co^{2+}$ as the chelated metal and palladium as the metal nanoparticle. The group R is a suitable linker, and varies between the CPG products. Both the binding of the palladium nanoparticles to the CPG material and the chelation of the cobalt ion to the 2,4-dihydroxyphenyl residue and the polyhistidine-tagged enzyme are schematically depicted.

In another embodiment, the immobilized enzyme material additionally comprises metal nanoparticles, such as nanoparticles of transition metals, such as, but not limited to, cobalt, nickel, or palladium. Material comprising metal nanoparticles can be for instance prepared by immersing amino-CPG or amino-HybCPG in a solution of an appropriate amount of metal salt, such as $CoCl_2$, $NiCl_2$, $Li_2PdCl_4$, $PdCl_2$ or $Pd(TFA)_2$, in acetonitrile or water, or in mixtures thereof. The metal ions are thereafter reduced to metal nanoparticles by the addition of an excess of appropriate reducing agent, such as sodium hydride, sodium borohydride, sodium cyanoborohydride, lithium aluminum hydride and the like. Upon addition of 2,4-dihydroxy-acetophenone, the initially formed imine is immediately reduced to the corresponding amine. After removal of the reducing agent by washing, a metal ion, such as $Co^{2+}$, $Fe^{3+}$ or $Ni^{2+}$, is then chelated on the matrix by suspension of the material in an aqueous solution of $CoCl_2$, $FeCl_3$ or $NiCl_2$, respectively. After drying, the obtained material can directly be used as a matrix for one or more polyhistidine-tagged enzymes; see FIG. 2.

While not wishing to be bound by theory, it is believed that the metal nanoparticles bind to the CPG material through the amino groups on the CPG material. It is also conceivable that the metal nanoparticles, formed by reduction of the metal ions, are of a size large enough to be entrapped in the pores of the CPG material.

The immobilized protein material containing both immobilized enzyme and metal nanoparticles can be applied as a heterogeneous biocatalyst in combined enzyme- and transition metal-catalyzed reactions. Examples of such reactions include, but are not limited to, dynamic kinetic resolution reactions. A specific example of such reactions is the dynamic kinetic resolution of amines by racemization of the amine by Pd nanoparticles followed by acylation with lipase, as shown in the appended examples.

Thus, in yet another aspect, the invention provides a method for catalyzing a combined enzyme-catalyzed and transition metal-catalyzed reaction. In this aspect the method comprises providing an immobilized protein material that additionally comprises transition metal nanoparticles, according to the invention, and bringing the said immobilized protein material into contact with at least one substrate upon which an enzyme and a transition metal, which are immobilized on the carrier, are capable of acting.

Examples of the immobilized protein material disclosed herein and the use of such material are described in the experimental section.

Definitions

The term "affinity tag" refers to a defined group, such as an organic or organometallic molecule, protein fragment or other, that is attached to a recombinant protein and that is able to bind to a specific group immobilized on a matrix. Examples of affinity tags are a polyhistidine tag, a glutathione S-transferase (GST) tag, a chitin binding protein (CBP) tag, a maltose binding protein (MBP) tag, a FLAG-tag, an avidin tag or a streptavidin tag. Affinity tags may also be referred to as fusion tags.

As used herein, the term "affinity-tagged protein" refers to a recombinant protein wherein an affinity tag, as defined above, has been added to the target protein. Affinity-tagged proteins can be prepared by recombinant DNA technology using methods known in the art, such as by ligation of DNA fragments or by PCR techniques. Affinity-tagged proteins may also be referred to as "fusion-tag proteins" or "fusion proteins".

The term "polyhistidine tag" refers to a string of at least two histidine residues, which is attached to the C- or N-terminal of a protein. The polyhistidine tag is preferably a string of at least six histidine residues. Other names commonly used for a polyhistidine tag are polyHis tag, histidine tag, hexahistidine-tag, 6xHis-tag and Hiss tag, as well as His-tag™. The term "polyhistidine-tagged enzyme" refers to a recombinant enzyme wherein the target enzyme is fused with a polyhistidine tag as defined above.

As used herein, the term "amino-CPG" refers to a CPG material which is functionalized with an amino group through an appropriate linker. The term "amino-HybCPG" as used herein refers to a Hybrid CPG material wherein the polymer coating contains amino groups.

The invention is further illustrated by means of the following examples, which do not limit the invention in any respect. All cited documents and references are incorporated herein by reference.

ABBREVIATIONS $a_w$ water activity
AlaDH alanine dehydrogenase from B. subtilis
CalA Candida antarctica lipase A (also known as Pseudozyma antarctica lipase A)
CalB Candida antarctica lipase B (also known as Pseudozyma antarctica lipase B)
DCM dichloromethane
2,5-DKCMO 2,5-diketocamphane monooxygenase from Pseudomonas putida
equiv. equivalent(s)
EtOAc ethyl acetate
FMN flavin mononucleotide
FRE flavin reductase from E. coli
GC gas chromatography
HEPES 4-(2-hydroxyethyl)piperazine-1-ethanesulfonic acid
IPTG isopropyl-β-D-thiogalactopyranoside
min minute(s)
MOPS 3-(N-morpholino)propanesulfonic acid
MTBE methyl tert-butyl ether (or tert-butyl methyl ether)
NADH nicotinamide adenine dinucleotide (reduced form)
PLP pyridoxal 5-phosphate
SDS-PAGE sodium dodecyl sulfate polyacrylamide gel electrophoresis
Tris tris(hydroxymethyl)aminomethane
ω-TA ω-transaminase from Chromobacterium violaceum
Experimental Methods The CPG materials were obtained from Prime Synthesis, Inc., (Aston, Pa., USA). The following controlled porosity glass materials were used in the examples:

LCAA CPG is a CPG derivatized with long chain alkyl amines (CPG-0502-N12).

Copoly-HybCPG-amine (in the following also referred to as "HybCPG copo") is a hybrid CPG coated with a co-polymer formed from 1:1 acrylonitrile:vinylbenzyl chloride and cross-linked in situ.

VBC HybCPG-amine (in the following also referred to as "HybCPG VBC") is a hybrid CPG coated with a polymer formed from vinylbenzyl chloride monomers and cross-linked in situ.

The (co-)polymers of the coatings are cross-linked with a bi-functional amine, as described in WO 2009/005631. The amino groups are thereafter introduced onto the chloropolymer coatings by reaction with sodium phthalimide followed by dephthaloylation with hydrazine.

The following porous organic polymers were used in the examples:

"Mid-Swell Polystyrene" (purchased from 3-Prime LLC, USA; Part Number 04-02-03-32), an amino functionalized polystyrene support. Pore size ~1000 Å (very broad distribution), particle size 100 μm, amine loading 222 μmol/g.

"Low-Swell Methacrylate Copolymer" (purchased from SPRIN Technologies S.p.A., Italy; Part number 1A02BN), an amino functionalized methacrylate support. Pore diameter unknown, particle size 100-300 μm, amine loading 270 μmol/g.

Cultivation of overexpressed ω-transaminase from Chromobacterium violaceum was performed as described in Cassimjee et al. (ACS Catal. 2011, vol. 1, pp. 1051-1055). Cultivation of overexpressed Candida antarctica lipase A was performed as described in Sandström et al. (Protein Eng Des Sel. 2009, vol 22, pp. 413-420). Cultivation of overexpressed Candida antarctica lipase B and CalB Trp104Ala, an unstable variant of lipase B, was performed as described in Engstrom et al. (Org. Biomol. Chem. 2011, vol. 9, pp. 81-82). Cultivation of overexpressed 2,5-diketocamphane monooxygenase from Pseudomonas putida was performed as described in Kadow et al. (AM B Express 2011, 1:13). Cultivation of overexpressed flavin reductase from E. coli was performed as described in Kadow et al. (Appl. Microbiol. Biotechnol. 2013, published online 5 Nov. 2013). Cultivation of overexpressed alanine dehydrogenase from B. subtilis was performed as described in Mutti et al. (Eur. J. Org. Chem. 2012, issue 5, pp. 1003-1007). When absent, a Hiss-tag was added to the genes by PCR. Polyhistidine-tagged CalA and CalB were immobilized on Accurel according to the procedures as described in Engstrom et al. (Org. Biomol. Chem. 2011, vol. 9, pp. 81-82).

EXAMPLES

Example 1

Preparation of Chelating CPG Carriers for Immobilization and Purification of Polyhistidine-Tagged Enzymes Amino-CPG (5 g) of desired type was treated with 2,4-dihydroxy acetophenone (1.5 equiv. to the amino functionalities of the CPG) in methanol (200 mL) with continuous stirring for 60 min. The formed imine was reduced by sequential addition of sodium borohydride (4 equiv.) with continuous stirring for 60 min. The solid material was filtered, rinsed with saturated aqueous sodium carbonate solution, water and then ethanol, and then dried at 80° C. for 2 h. The particles were then immersed in a saturated aqueous solution of $CoCl_2$ (100 mL). After filtration and rinsing with water and ethanol, the particles were dried at 80° C. for 2 h. The properties of the different chelating CPG carriers are shown in Table 1.

TABLE 1

| Chelating CPG carrier | Porosity[1] (Å) | Amino derivatization[3] (μmol/g) | Cobalt(II) loading[4] (μmol/g) |
|---|---|---|---|
| LCAA CPG ($Co^{2+}$) | 533 | 166 | 2.8 |
| HybCPG VBC ($Co^{2+}$) | 526[2] | 398 | 18.7 |
| HybCPG copo ($Co^{2+}$) | 590[2] | 360 | 25.5 |

[1]Measured by mercury porosimetry.
[2]Measured prior to coating with the crosslinked polymer; the accessible pore diameter of the HybCPG is reduced by 160-200 Å after coating.
[3]Nitrogen content before preparation of enzyme-bound CPG according to Scheme 1.
[4]Elemental analysis of the chelating CPG without bound enzyme.

Carriers containing $Fe^{3+}$ as the chelated metal ion were prepared similar to the procedure above, but using an aqueous solution of $FeCl_3$ instead of $CoCl_2$.

Example 2

Preparation of Chelating Porous Polystyrene and Polymethacrylate Carriers for Immobilization and Purification of Polyhistidine-Tagged Enzymes Washed (water/ethanol 1:1, 400 mL) and dried (vacuum 16 h after filtration) amino functionalized porous organic polymer particles (2 g) of desired type (see below) was treated with 2,4-dihydroxy acetophenone (1.5 equiv. to the amino functionalities of the plastic) in methanol (50 mL) with continuous stirring for 60 min. The formed imine was reduced by sequential addition of sodium borohydride (4 equiv.) with continuous stirring for 60 min. The solid material was filtrated, rinsed with saturated aqueous sodium carbonate solution, water and then ethanol, and then dried in vacuum at 25° C. for 16 h.

The particles were then immersed in a saturated aqueous solution of $CoCl_2$ (100 mL). After filtration and rinsing with water and ethanol, the particles were dried in vacuum at 25° C. for 16 h. The properties of the different chelating porous plastic carriers are shown in Table 2.

TABLE 2

| Chelating porous plastic carrier | Amino derivatisation (as stated by the manufacturer, µmol/g) | Cobalt(II) loading (elemental analysis, µmol/g) |
|---|---|---|
| Polystyrene ($Co^{2+}$) | 222 | 67 |
| Polymethacrylate ($Co^{2+}$) | 270 | 24 |

Example 3

Immobilization of Polyhistidine-Tagged Enzymes on Chelating Carriers

The cell culture supernatants containing CalA or CalB were used without buffering. The cell lysates of ω-TA were prepared by cell resuspension in HEPES buffer (50 mM, 500 mM NaCl, pH 8.3). After addition of detergents (BugBuster™ 10X, Novagen), cell debris was removed by centrifugation. The chelating CPG carrier was immersed in the lysates or supernatants followed by stirring on an orbital shaker (150 rpm). Bradford analyzed samples of the solutions during immobilization confirmed the completion of the binding and saturation of the chelating CPG carrier as the protein concentration seized to decrease. Activity assays were also performed with the solutions after removal of the CPG carrier by filtration. The immobilized preparations were then rinsed with buffer (MOPS 50 mM, pH 7.4) for CalA and CalB; HEPES (see above) for ω-TA) and dried under vacuum for 16 h.

Extraction of immobilized enzyme from the CPG carrier was performed by immersing the particles in elution buffer (50 mM sodiumphosphate, 500 mM imidazole, pH 7.5) and incubation on an orbital shaker for 20 min. The presence and purity of the extracted enzymes were visualized by SDS-PAGE; only bands corresponding to the Hiss-tagged enzymes were visible.

Active site quantification of ω-TA in solvent was performed as previously described (Cassimjee et al., ACS Catal. 2011, vol. 1, pp. 1051-1055). Active site quantification of immobilized ω-TA in solvent was performed by adding ω-TA-CPG to 1-phenylethylamine (1 mM, 1 mL, MTBE $a_w$=0.6, 1 mM pentadecane). The reaction mixture was stirred on an orbital shaker (150 rpm, 24 h, 22° C.). The water activity of the solvent was set by salt hydrate pairs ($Na_2HPO_4$, $2H_2O/7H_2O$) but not controlled after addition of the ω-TA-CPG or during the reaction. Conversions were measured by GC (200 µL samples to EtOAc, 3 drops of acetic anhydride and triethylamine, 8 h incubation at 22° C.), with pentadecane as internal standard.

Active site quantification of immobilized ω-TA in buffer was performed by adding ω-TA-CPG to 1-phenylethylamine (1 mM, 1 mL, 50 mM HEPES, pH 7.0). The reaction mixture was stirred on an orbital shaker (150 rpm, 24 h, 22° C.). Samples (400 µL) were treated with aqueous NaOH solution (1%), extracted with DCM and analyzed by GC after addition of pentadecane (1 mM, EtOAc). The conversions were in all cases compared to blank reactions with the chelating CPG (no enzyme bound).

The yield of immobilization, i.e. the amount of active enzyme removed from the lysate versus the amount of active enzyme retained on the CPG after washing, was more than 99% based on active site quantification. The results are shown in Table 3.

TABLE 3

| CPG carrier | Immobilization yield (% active enzyme in MTBE) | Loading, active sites in MTBE (% w/w) | Loading, active sites in buffer[1] (% w/w) |
|---|---|---|---|
| LCAA CPG ($Co^{2+}$) | >99% | 24 | 19 |
| HybCPG VBC ($Co^{2+}$) | >99% | 29 | 25 |
| HybCPG copo ($Co^{2+}$) | >99% | 21 | 13 |

[1]No PLP was added after immobilization.

Immobilization of polyhistidine-tagged enzymes (CalA and CalB) on chelating porous polystyrene and polymethacrylate carriers was performed as described above for CPG carriers.

Example 4

Use of ω-TA-CPGs as Catalyst

The ω-TA-CPGs prepared in Example 3 were applied as catalysts in the enantiospecific transamination of phenoxy-2-propanone:

20 mg of ω-TA-CPG was added to a solution of 3 mL of MTBE ($a_w$=0.6) with 100 mM racemic 1-phenylethylamine and 50 mM 2-phenoxypropanone, and the reaction mixture was incubated with orbital shaking (150 rpm) at 50° C. Pentadecane (50 mM) was used as an internal standard. The conversion and enantiomeric excess of 1-phenylethylamine was followed by chiral gas chromatography after taking samples (50 µL) at recorded time points; the samples were derivatized with acetic anhydride and triethyl amine as described above. The formation of 1-phenoxypropan-2-amine was measured without derivatisation. The results are shown in Table 4.

TABLE 4

| Enzyme | Activity in MTBE[1] (μmol/min/g CPG) | Activity in MTBE[1] (μmol/min/g active enzyme) |
|---|---|---|
| ω-TA-LCAA CPG (Co$^{2+}$) | 0.38 | 1.58 |
| ω-TA-HybCPG VBC (Co$^{2+}$) | 0.70 | 2.41 |
| ω-TA-HybCPG copo (Co$^{2+}$) | 0.06 | 0.29 |

[1]Initial rate of the reaction

Example 5

Use of Immobilized CalA and CalB as Catalysts

The CalA-CPGs, CalB-CPGs, CalB-polystyrene and CalB-polymethacrylate prepared in Example 3 were applied as catalysts in the enantioselective acylation of 1-phenylethanol (a kinetic resolution):

Lipase catalyzed kinetic resolution reactions were performed by addition of the immobilized enzyme (20 mg) to a solution of 3 mL of toluene ($a_w$=0.1) with 10 mM 1-phenylethanol and 100 mM vinyl butyrate, and the mixture was incubated with orbital shaking (200 rpm) at 22° C. (for CalA and CalB) or 50° C. (for CalB Trp104Ala). Pentadecane (5 mM) was used as an internal standard. The conversion and enantiomeric excess of 1-phenylethanol and 1-phenylethyl butyrate were measured by chiral GC by taking samples (50 μL) at recorded time points.

The following reactions were included for comparison:

CalB immobilized on Accurel®, a porous polypropylene powder.

CalB immobilized on amino-HybCPG copo in unmodified form (i.e. not processed according to Example 1).

Immobilization of CalB (and CalB Trp104Ala) on ethanol activated Accurel® (Accurel MP1001, particle size <1000 μm, Membrana GmbH, Wuppertal, Germany) was performed by adding the porous material to concentrated supernatant in a ratio of 50:1 to the amount of enzyme (protein content was measured by the Bradford method), followed by incubation for at least eight hours. The results are shown in Table 5.

TABLE 5

| Enzyme | Bulk density[1] (g/cm$^3$) | $E^{app}$ | Activity in toluene[2] (μmol/min/g) | Bulk volumetric activity in toluene (μmol/min/cm$^3$) |
|---|---|---|---|---|
| CalB-LCAA CPG (Co$^{2+}$) | 0.28 | >300 (R) | 0.83 | 0.23 |
| CalB-HybCPG VBC (Co$^{2+}$) | 0.23 | >300 (R) | 0.90 | 0.21 |
| CalB-HybCPG copo (Co$^{2+}$) | 0.245 | >300 (R) | 1.08 | 0.26 |
| CalB-Accurel ® | 0.10 | >300 (R) | 5.99 | <0.60[3] |
| CalB Trp104Ala-LCAA CPG (Co$^{2+}$) | 0.28 | n/a | n/d | n/d |
| CalB Trp104Ala-VBC HybCPG (Co$^{2+}$) | 0.23 | 1.3 (R) | 0.19 | 0.04 |
| CalB Trp104Ala-HybCPG copo (Co$^{2+}$) | 0.245 | 1.0 | 0.04 | 0.01 |
| CalB Trp104Ala-Accurel ® | 0.10 | 7.1 (R) | 0.23 | <0.023 |
| CalB + Amino-HybCPG copo[4] | 0.245 | >300 (R) | 0.36 | 0.083 |
| CalA-LCAA CPG (Co$^{2+}$) | 0.28 | 1.3 (R) | 16.18 | 4.53 |
| CalB-polystyrene (Co$^{2+}$) | n/d | >300 (R) | 0.068 | n/d |
| CalB-polymethacrylate (Co$^{2+}$) | n/d | >300 (R) | 0.174 | n/d |

[1]Dry carriers before binding of enzyme.
[2]Initial rate of consumption of 1-phenylethanol.
[3]Without inclusion of swelling which occurs in contact with solvent.
[4]amino-HybCPG copo was used without modification.

Example 6

Preparation of Cascade-CPG with Three Different Enzymes ("BV-cascade-CPG")

The cell lysates of 2,5-DKCMO, FRE and AlaDH were prepared by cell resuspension in sodium phosphate buffer (50 mM, 500 mM NaCl, pH 7.5) and addition of Bug-Buster™ 10X. After centrifugation and removal of cell debris, the chelating Co$^{2+}$ CPG carrier was immersed in a mixture of equal volumes of the three cell lysates, followed by stirring on an orbital shaker (150 rpm). Bradford analyzed samples of the solutions during immobilization confirmed the completion of the binding and saturation of the CPG carrier as the protein concentration seized to decrease. Activity assays were also performed with the solutions after removal of the CPG by filtration. The immobilized preparations were then rinsed with sodium phosphate buffer (see above) and then dried under vacuum for 16 h.

Example 7

Enzymatic Cascade Reaction using BV-Cascade-CPGs as Catalysts

The cascade-CPGs prepared in Example 6 were applied as catalysts in the Baeyer-Villiger oxidation of (+)-camphor:

65 mg BV-cascade-CPG was added to a reaction mixture of phosphate buffer (100 mM, pH 7.5) with 2.0 mM (+)-camphor, 5.0 mM L-alanine, 0.3 mM FMN and 0.5 mM NADH with a total liquid volume of 5.0 mL. Oxygen was then dissolved (bubbling for 30 s) followed by sealing of the vessel; the mixture was incubated on an orbital shaker (150 rpm) at 22° C. Samples (500 µL) were extracted to EtOAc with ethylbenzoate as internal standard and analyzed by GC. The conversion was measured after 3 hours. Oxygen was added after 24 hours and the reaction was allowed to continue for an additional 3 hours, after which the conversion was measured again (27 h).

A comparative reaction with free (non-immobilized) 2,5-DKCMO, FRE and AlaDH (from cell lysates) was also performed. The proportions and amounts of the enzymes were not measured. The results are shown in Table 6.

TABLE 6

| Enzyme | Conversion after 3 h | Conversion after 24 h | Conversion after 27 h[1] |
|---|---|---|---|
| BV-cascade-LCAA CPG ($Co^{2+}$) | <5% | <5% | <5% |
| BV-cascade-HybCPG VBC ($Co^{2+}$) | 63% | 63% | 88% |
| 2,5-DKCMO, FRE, AlaDH (free, non-immobilized enzymes) | 65% | 65% | 65% |

[1]With re-addition of oxygen after 24 hours

Multi-phase reactions were performed by adding 1.0 g BV-cascade-CPG to a reaction mixture of phosphate buffer (100 mM, pH 7.5) with 160 mM L-alanine, 0.3 mM FMN and 0.5 mM NADH with a total liquid volume of 5.0 mL. 5 mL cyclohexane with (+)-camphor (100 mM) was then added as a second liquid phase. The sealed vessel was stirred on an orbital shaker (100 rpm) at 22° C. with continuous oxygen addition to the aqueous phase. Samples (50 µL) from the organic phase were taken at recorded time points and analyzed by GC after addition of ethylbenzoate (2.0 mM in EtOAc) as internal standard. The conversion after 72 h was measured after extraction of all components with EtOAc (20 mL).

A comparative reaction with free (non-immobilized) 2,5-DKCMO, FRE and AlaDH (from cell lysates) was also performed. The proportions and amounts of the enzymes were not measured. The results are shown in Table 7.

TABLE 7

| Enzyme | Conversion after 72 h |
|---|---|
| BV-cascade-LCAA CPG ($Co^{2+}$) | <5% |
| BV-cascade-HybCPG VBC ($Co^{2+}$) | 56% |
| 2,5-DKCMO, FRE, AlaDH (free, non-immobilized enzymes) | <5% |

Example 8

Preparation of Cascade-CPG with CalB and Pd-Nanoparticles ("Pd-CalB-CPG")

Amino-CPG (5 g) was immersed in a solution of $Pd(TFA)_2$ (0.5 equiv. to the amino functionalities of the CPG) in water (200 mL) and the mixture was continuously stirred for 10 min. $NaBH_4$ (7 equiv.) was then added and the mixture was stirred for an additional 30 min. 2,4-Dihydroxyacetophenone (0.5 equiv.) was then added, after which the mixture was stirred for 30 min. The solid material was filtrated and thoroughly rinsed with water, and then immersed in a saturated aqueous solution of $CoCl_2$ (100 mL). After filtration and washing with water, the solid material was immersed in a solution of polyhistidine-tagged CalB (purified or from supernatant) and stirred for 30 min. The immobilized preparation was then filtrated, rinsed with buffer (20 mM MOPS, pH 7.4) and thereafter dried under vacuum for 16 h.

Example 9

Cascade Reaction Using Pd-CalB-CPGs

The material prepared in Example 8 was applied as a catalyst in the enantioselective acylation of 1-phenylethylamine (a dynamic kinetic resolution):

100 mg of the Pd-CalB-CPG was immersed in a solution of 1.0 mL toluene containing 20 mM racemic 1-phenylethylamine and 100 mM isopropyl butyrate. 1 mg $NaBH_4$ was added and the reaction vesicle was sealed. The system was incubated at 65° C. with continuous stirring on an orbital shaker (100-800 rpm) for 24 to 48 h. The conversion and enantiomeric excess of the substrate and product (e.g. (R)—N-(1-phenylethyl)butyramide) were measured by chiral GC by taking samples at recorded time points.

The product is obtained by separation of the phases, shaking the organic phase with 1 N HCl (three times) in order to remove residual acyl donor and amine, and then back extraction of the washing phases with EtOAc. The combined organic phases are evaporated in vacuo to yield the product, which is further purified by flash chromatography.

Example 10

A. Determination of Metal Ion Leaching

To determine the amount of metal ion that leaches from the carrier at given conditions, carriers based on CPG and HybCPG and containing either $Co^{2+}$ or $Fe^{3+}$ were subjected to prolonged incubation in aqueous buffer.

250 mg each of LCAA CPG, HybCPG VBC and HybCPG copo, with either bound $Co^{2+}$ or $Fe^{3+}$, were subjected to incubation in 3 mL of aqueous buffer (HEPES 20 mM, pH 7.0) for 72 h on a shaking table at room temperature.

The amount of $Co^{2+}$ was measured by mixing one part of the incubated solution with one part $NH_4SCN$-solution (1.0 M), one part HCl-solution (6.0 M) and two parts of acetone. This procedure reveals a blue colour proportional to the concentration of $Co^{2+}$, which was quantified by spectrophotometry at 620 nm. A blank sample with the buffer alone was also tested.

The amount of $Fe^{3+}$ was measured by mixing one part of the incubated solution with one part $NH_4SCN$-solution (1.0 M) and one part HCl-solution (6.0 M). This procedure reveals a red colour proportional to the concentration of $Fe^{3+}$, which was quantified by spectrophotometry at 480 nm. A blank sample with the buffer alone was also tested.

After removing one half of the solutions (1.5 mL) from the incubated carrier materials, 1.5 mL of 6.0 M HCl-solution was added and the materials were incubated on the shaker for 1 h; this procedure effectively desorbs all bound metal ions. One part of this incubated solution was then mixed with one part HCl-solution (3 M) and one part $NH_4SCN$-solution (1.0 M). To the samples where $Co^{2+}$ was to be quantified, two parts of acetone was also added. The absorbance at 620 nm for $Co^{2+}$ quantification, and at 480 nm for $Fe^{3+}$ quantification was recorded. Based on the absorbance measurements, values corresponding to the total amount of metal ions were calculated for the tested volumes at the two different incubations (first at pH 7.0 and then in 3.0 M HCl), and corrected for the removed volume (1.5 mL after the first incubation). The fraction of leached metal ions at pH 7.0 could thereby be quantified. The results are presented in Table 8 below.

TABLE 8

| Carrier | Leached metal ions after 72 h at pH 7.0 (%) |
| --- | --- |
| LCAA CPG ($Co^{2+}$) | 16 |
| HybCPG VBC ($Co^{2+}$) | 14 |
| HybCPG copo ($Co^{2+}$) | 7.0 |
| LCAA CPG ($Fe^{3+}$) | 1.5 |
| HybCPG VBC ($Fe^{3+}$) | 0.36 |
| HybCPG copo ($Fe^{3+}$) | 0.61 |

It can be seen that $Fe^{3+}$ bound to CPG and HybCPG carrier material is less prone to leaching than $Co^{2+}$.

B. Determination of Enzyme Leaching

To determine the amount of enzyme that dissociates from the carrier at given conditions, immobilized preparations of ω-TA on CPG or HybCPG were subjected to prolonged incubation in aqueous buffer.

12-16 mg each of ω-TA-LCAA CPG, ω-TA-HybCPG VBC and ω-TA-HybCPG copo, wherein the enzyme is bound by either $Co^{2+}$ or $Fe^{3+}$, were incubated in 4 mL of aqueous buffer (HEPES 100 mM, pH 7.0) for 1 min on an orbital shaker. After this time, no enzyme could be detected in the solution. This was measured by activity assay, in which 1 mL of the solution was used after sedimentation of the immobilized material. The preparations with the remaining 3 mL were incubated for 24 h on the orbital shaker, after which some of the preparations displayed measureable amounts of enzyme in the solution.

The activity assay was performed by taking 1 mL of the solution, adding 1 mL assay mixture (1-phenylethylamine (10 mM), sodiumpyruvate (5 mM) and PLP (1 µM), dissolved in the same buffer), and measuring the absorbance change over time at 245 nm for 5 min. A blank reaction with pure buffer was also tested. At this wavelength the formation of acetophenone, a product from the transamination reaction, can be monitored as an increase of absorbance with an extinction coefficient of 12 $mM^{-1}cm^{-1}$ (Schatzle et al., Anal. Chem. 2009, vol. 81, pp. 8244-8248). Since the kinetic constants are known (Cassimjee et al., Org. Biomol. Chem. 2012, vol. 10, pp. 5466-5470), the amount of leached enzyme can be calculated. Before the leaching experiment, the amount of bound enzyme in the immobilized preparations was measured by active site quantification. The amount of leaching after 24 h for each material is shown in Table 9.

TABLE 9

| Material | Leached enzyme after 24 h at pH 7.0 (%) |
| --- | --- |
| ω-TA-LCAA CPG ($Co^{2+}$) | 7.9 |
| ω-TA-HybCPG VBC ($Co^{2+}$) | 0.4 |
| ω-TA-HybCPG copo ($Co^{2+}$) | n/d |
| ω-TA-LCAA CPG ($Fe^{3+}$) | 3.4 |
| ω-TA-HybCPG VBC ($Fe^{3+}$) | n/d |
| ω-TA-HybCPG copo ($Fe^{3+}$) | n/d |

The values show that at the tested conditions, $Fe^{3+}$ as chelated metal ion results in less enzyme leaching. HybCPG copo as the carrier did not result in any detectable enzyme leaching at the chosen conditions with either $Co^{2+}$ or $Fe^{3+}$ as chelated metal ion. LCAA CPG, which has a glass surface, gave the highest amount of enzyme leaching. This may be the result of unspecific enzyme binding to the glass surface.

Example 11

Purification of Polyhistidine-Tagged ω-TA with HybCPG copo ($Co^{2+}$)

Cell lysate (5.0 mL) from a pelleted IPTG-induced 24 h cultivation of ω-TA in 100 mL Luria-Bertani medium with addition of 50 µg/mL kanamycin was prepared by use of BugBuster™. An excess of co-enzyme (PLP) was added and the solution was incubated at 37° C. for 1 h. Excess PLP (not bound by the enzyme) was then removed by buffer change, using a PD10 column (two rounds), to a HEPES buffer (50 mM, 500 mM NaCl, pH 8.2 (Buffer 1)), which gave 7.0 mL of solution containing the target holoenzyme, native proteins and other impurities A column was filled with 204 mg HybCPG copo ($Co^{2+}$) containing 26 µmol/g $Co^{2+}$. The material was pre-wetted by adding 7.0 mL of Buffer 1, and the flow-through was discarded.

Active holoenzyme is spectrophotometrically measured at 395 nm, ε=8.1 $mM^{-1}cm^{-1}$ (Cassimjee et al., ACS Catal. 2011, vol. 1, pp. 1051-1055). Following absorbance measurement, the lysate was added to the column, and the flow-through was collected. The absorbance difference at this wavelength of the lysate before and after passing through the column was measured to 0.62 (all measurements performed with 1.0 cm path length). This corresponds to 29 mg of enzyme, now bound to the HybCPG copo ($Co^{2+}$) carrier in the column.

The column was then washed with 7.0 mL of Buffer 1. The flow-through was collected of which the absorbance was measured to 0.11, with Buffer 1 as blank. This corresponds to 5 mg of enzyme that was washed away from the column, assumingly due to unspecifically bound or unbound enzyme, leaving 24 mg bound enzyme in the column.

Dissociation of the bound enzyme in the column was performed by applying 5.0 mL of Tris buffer (50 mM, 500 mM imidazole, pH 7.5 (Buffer 2)). The flow-through was collected and an excess of co-enzyme was again added. As described above, excess PLP was removed by buffer change, using a PD10 column, to Buffer 1, giving a total volume of 7.0 mL of solution with dissolved holoenzyme. The absorbance was measured to 0.465. This corresponds to 22 mg of purified enzyme, or a yield of 92%. The solution appeared significantly cleared of contaminating host-cell protein, which was also confirmed by SDS-PAGE.

The invention claimed is:

1. An immobilized enzyme material comprising a carrier and at least one enzyme immobilized on the carrier, wherein the carrier comprises a carrier material to which an affinity matrix is attached, the carrier material being chosen from the group consisting of:
   (a) controlled porosity glass (CPG) having a pore size of 10 to 300 nm; and
   (b) hybrid controlled porosity glass (Hybrid CPG) having a pore size of 10 to 300 nm;
   and wherein:
   the at least one enzyme contains an affinity tag and is immobilized on the carrier through specific affinity binding to the affinity matrix;
   the affinity tag is a polyhistidine tag;
   the affinity matrix contains a chelated metal ion; and
   catalytic activity of the enzyme is maintained.

2. The immobilized enzyme material according to claim 1, wherein the carrier material is controlled porosity glass (CPG).

3. The immobilized enzyme material according to claim 1, wherein the carrier material is hybrid controlled porosity glass (Hybrid CPG).

4. The immobilized enzyme material according to claim 1, wherein the chelated metal ion is $Co^{2+}$.

5. The immobilized enzyme material according to claim 1, wherein the chelated metal ion is $Fe^{3+}$.

6. The immobilized enzyme material according to claim 1, comprising two or more immobilized enzymes.

7. The immobilized enzyme material according to claim 1, in addition comprising metal nanoparticles.

8. The immobilized enzyme material according to claim 7, wherein the metal nanoparticles are transition metal nanoparticles.

9. The immobilized enzyme material according to claim 7, wherein the metal nanoparticles are selected from the group consisting of cobalt, nickel, and palladium nanoparticles.

10. The immobilized enzyme material according to claim 1, wherein the at least one enzyme comprises a hydrolase.

11. The immobilized enzyme material according to claim 1, wherein the at least one enzyme comprises an oxidoreductase.

12. The immobilized enzyme material according to claim 1, wherein the at least one enzyme comprises a transferase.

13. A method for the preparation of the immobilized enzyme material according to claim 1, the method comprising:
   (i) providing a carrier material containing amino groups, the carrier material containing amino groups being chosen from the group consisting of:
      (a) controlled porosity glass (CPG) having a pore size of 10 to 300 nm; and
      (b) hybrid controlled porosity glass (Hybrid CPG) having a pore size of 10 to 300 nm;
   (ii) reacting the carrier material containing amino groups with 2,4-dihydroxyacetophenone, thereby linking a dihydroxyphenyl group to the carrier material containing amino groups;
   (iii) forming a chelate complex between the dihydroxyphenyl group and a metal ion capable of binding a polyhistidine-tagged protein, thereby obtaining the carrier material to which the affinity matrix is attached; and
   (iv) binding the enzyme to the carrier material comprising the metal ion, wherein the enzyme is a polyhistidine-tagged enzyme.

14. The method according to claim 13, in addition comprising binding a transition metal nanoparticle to the carrier material.

15. A method for the immobilization of at least one enzyme, comprising immobilizing the at least one enzyme to a carrier material to which an affinity matrix is attached, the carrier material being chosen from the group consisting of:
   (a) controlled porosity glass (CPG) having a pore size of 10 to 300 nm; and
   (b) hybrid controlled porosity glass (Hybrid CPG) having a pore size of 10 to 300 nm;
   and wherein:
   the at least one enzyme, contains an affinity tag and is immobilized on the carrier through specific affinity binding to the affinity matrix;
   the affinity tag is a polyhistidine tag;
   the affinity matrix contains a chelated metal ion; and
   catalytic activity of the enzyme is maintained.

16. The method according to claim 15, wherein the carrier material is controlled porosity glass (CPG).

17. The method according to claim 15, wherein the carrier material is hybrid controlled porosity glass (Hybrid CPG).

18. The method according to claim 15, wherein the chelated metal ion is $Co^{2+}$.

19. The method according to claim 15, wherein the chelated metal ion is $Fe^{3+}$.

20. A method for catalyzing an enzyme-catalyzed reaction, comprising providing the immobilized enzyme material according to claim 1, and bringing the immobilized enzyme material into contact with at least one substrate upon which the enzyme, which is immobilized on the carrier material, is capable of acting.

* * * * *